United States Patent
Hegazi et al.

(10) Patent No.: US 9,028,753 B2
(45) Date of Patent: May 12, 2015

(54) MULTI-CUVETTE AUTOSAMPLER FOR PHOTO-OPTICAL MEASUREMENTS

(71) Applicant: Saudi Arabian Oil Company, Dhahran (SA)

(72) Inventors: Ezzat Hegazi, Dhahran (SA); Christoph Stamm, Winterthur (CH); Peter Engel, Winterthur (CH); Benjamin Fellmann, Winterthur (CH); Hanspeter Sautter, Winterthur (CH)

(73) Assignees: Saudi Arabian Oil Company, Dhahran (SA); Zurich University of Applied Sciences, Winterthur (CH)

( * ) Notice: Subject to any disclaimer, the term of this patent is extended or adjusted under 35 U.S.C. 154(b) by 278 days.

(21) Appl. No.: 13/666,318

(22) Filed: Nov. 1, 2012

(65) Prior Publication Data
US 2013/0107251 A1    May 2, 2013

Related U.S. Application Data

(60) Provisional application No. 61/554,195, filed on Nov. 1, 2011.

(51) Int. Cl.

| | |
|---|---|
| *G01N 21/00* | (2006.01) |
| *G01N 31/00* | (2006.01) |
| *G01N 33/00* | (2006.01) |
| *G01N 21/13* | (2006.01) |
| *G01N 1/10* | (2006.01) |
| *G01N 35/04* | (2006.01) |

(Continued)

(52) U.S. Cl.
CPC ........ *G01N 21/13* (2013.01); *G01N 2035/0401* (2013.01); *G01N 2035/0444* (2013.01); *G01N 35/025* (2013.01); *G01N 35/1011* (2013.01)

(58) Field of Classification Search
CPC . G01N 21/13; G01N 35/1011; G01N 35/025; G01N 2035/0401; G01N 2223/307
See application file for complete search history.

(56) References Cited

U.S. PATENT DOCUMENTS

| 3,623,381 A | 11/1971 | Crepin | |
|---|---|---|---|
| 3,748,044 A * | 7/1973 | Liston | ........................... 356/409 |

(Continued)

FOREIGN PATENT DOCUMENTS

| EP | 0681606 A | 11/1995 |
|---|---|---|
| EP | 1227313 A2 | 7/2002 |
| WO | 2006/102348 A1 | 9/2006 |

OTHER PUBLICATIONS

PCT Notification of Transmittal of the International Search Report and the Written Opinion of the International Searching Authority, or the Declaration; dated Feb. 26, 2013; International Application No. PCT/US2012/063002; International File Date: Nov. 1, 2012.

*Primary Examiner* — Jill Warden
*Assistant Examiner* — Julie Tavares
(74) *Attorney, Agent, or Firm* — Bracewell & Giuliani LLP; Constance Gall Rhebergen

(57) ABSTRACT

A motorized multi-cuvette rotatable carousel positions cuvettes around a stationary axis. A rotatable cuvette holder plate positions cuvettes in the carousel. The cuvette holder plate has spring tensioning elements that hold cuvettes in a precise position within the cuvette holder plate. A cuvette positioning arm is attached to the rotatable carousel assembly. The positioning arm geometrically positions the cuvette for depth-resolved laser-induced fluorescence testing.

17 Claims, 8 Drawing Sheets

(51) Int. Cl.
*G01N 35/02* (2006.01)
*G01N 35/10* (2006.01)

(56) References Cited

U.S. PATENT DOCUMENTS

| | | | |
|---|---|---|---|
| 4,535,585 A * | 8/1985 | Gardos | 53/247 |
| 6,106,781 A * | 8/2000 | Rosenberg | 422/64 |
| 7,731,899 B2 | 6/2010 | Talmer et al. | |
| 7,830,518 B2 | 11/2010 | Kanayama | |
| 7,939,036 B2 | 5/2011 | Burkhardt et al. | |
| 8,064,061 B2 | 11/2011 | Yamamoto et al. | |
| 2010/0111766 A1 | 5/2010 | Wang et al. | |
| 2010/0150779 A1 | 6/2010 | Chow et al. | |
| 2011/0014085 A1 | 1/2011 | Yanami et al. | |
| 2011/0091986 A1 | 4/2011 | Nuotio et al. | |
| 2011/0293475 A1 | 12/2011 | Rosenberg et al. | |

* cited by examiner

MULTI-CUVETTE AUTOSAMPLER FOR PHOTO-OPTICAL MEASUREMENTS

CROSS REVERENCE TO RELATED APPLICATIONS

This application claims priority to and the benefit of U.S. Provisional Application Ser. No. 61/554,195, filed Nov. 1, 2011, the full disclosure of which is hereby incorporated by reference herein.

BACKGROUND OF THE INVENTION

1. Field of the Invention

The present invention relates to photo-optical measurement of cuvette contained samples, and more particularly to precise positioning of cuvettes in a multi-cuvette system, the samples undergoing depth-resolved laser-induced fluorescence testing.

2. Description of the Related Art

Depth-resolved laser-induced fluorescence measurement has seen use measuring concentrations of fuel mixtures. Measurements involve illuminating a sample with a laser and measuring the fluorescent emissions of the sample. Such an apparatus is often set up for the testing of individual samples. Industry usage of such a technique often requires the ability to quickly test many samples in an efficient manner. While the previous apparatus and methods provide excellent results, it would be advantageous to accurately illuminate multiple samples in a time efficient manner.

There exist a number of systems for handling of biological or other samples for multi-sample testing. These systems often have specific biological purposes and the level of precision in the handling of samples can vary greatly between systems. Further, there exist many auto sampling systems carrying multiple sample containers. These systems often suffer from accuracy and repeatability issues as they do not address the considerations of the precise positioning of individual sample containers for repeatable position testing of multiple samples. It would be advantageous to develop a system that ensures precise positioning and therefore establishes repeatability of testing multiple samples.

Other auto sampling systems consist of multi-sample containers or multi-sample cards that carry the individual samples in a plurality of sample test sites within one container. These systems may employ fluorescence or other testing where the multiple samples in the sample containers may be illuminated and tested simultaneously. These multi-sample based container management systems lack elements that provide a precise geometric location of the sample being tested. It would be advantageous to provide a system that addresses the precise geometric location of the sample.

Many multiple sample testing systems exist. Often the systems have similar limitations to the systems described above, such as: a system useful for testing only one sample at a time; a multi-sample system that does not have elements providing for the precise geometric location of a sample within the testing apparatus; and a multi-sample system that does not provide for geometric positioning of a sample beyond the apparatus conveying the sample. The present invention seeks to improve upon the described systems by addressing these issues as well as others.

SUMMARY OF THE INVENTION

The current invention provides a cuvette positioning system that is efficient and accurate for performing depth-resolved laser-induced fluorescence measurements on cuvette-contained industrial fluid samples. Fluid samples can include gas, liquid, or combination gas and liquid cuvette-contained samples. This cuvette positioning system can additionally be applied to other sample types, can use other light sources and can be used for other photo-optical measurements such as absorption, transmission and interferometry.

In one embodiment of the invention, the cuvette positioning system provides an apparatus for positioning cuvettes into precise geometrical positions within a photo-optical measuring station. The apparatus comprises a rotatable carousel assembly for carrying multiple cuvettes in a loose-fitting manner and a separate positioning arm assembly for locking the cuvettes, individually, in the same precise orientation and location with respect to a precisely positioned slit for use in comparative photo-optical measurements. The apparatus additionally comprises a linear stage that permits the whole rotatable carousel assembly and the positioning arm assembly to be moved along a linear axis in relation to the fixed slit. The apparatus makes it possible to perform absolute and comparative photo-optical measurements on multiple samples in different selectable depths, the depths being sufficiently precise for photo-optical measurements such as depth-resolved laser-induced fluorescence measurements.

BRIEF DESCRIPTION OF THE DRAWINGS

So that the manner in which the above-recited features, aspects and advantages of the invention, as well as others that will become apparent, are attained and can be understood in detail, more particular description of the invention briefly summarized above may be had by reference to the embodiments thereof that are illustrated in the drawings that form a part of this specification. It is noted, however, that the appended drawings illustrate only preferred embodiments of the invention that are, therefore, not to be considered limiting of the invention's scope, for the invention may admit to other equally effective embodiments.

DETAILED DESCRIPTION

Figure 1:
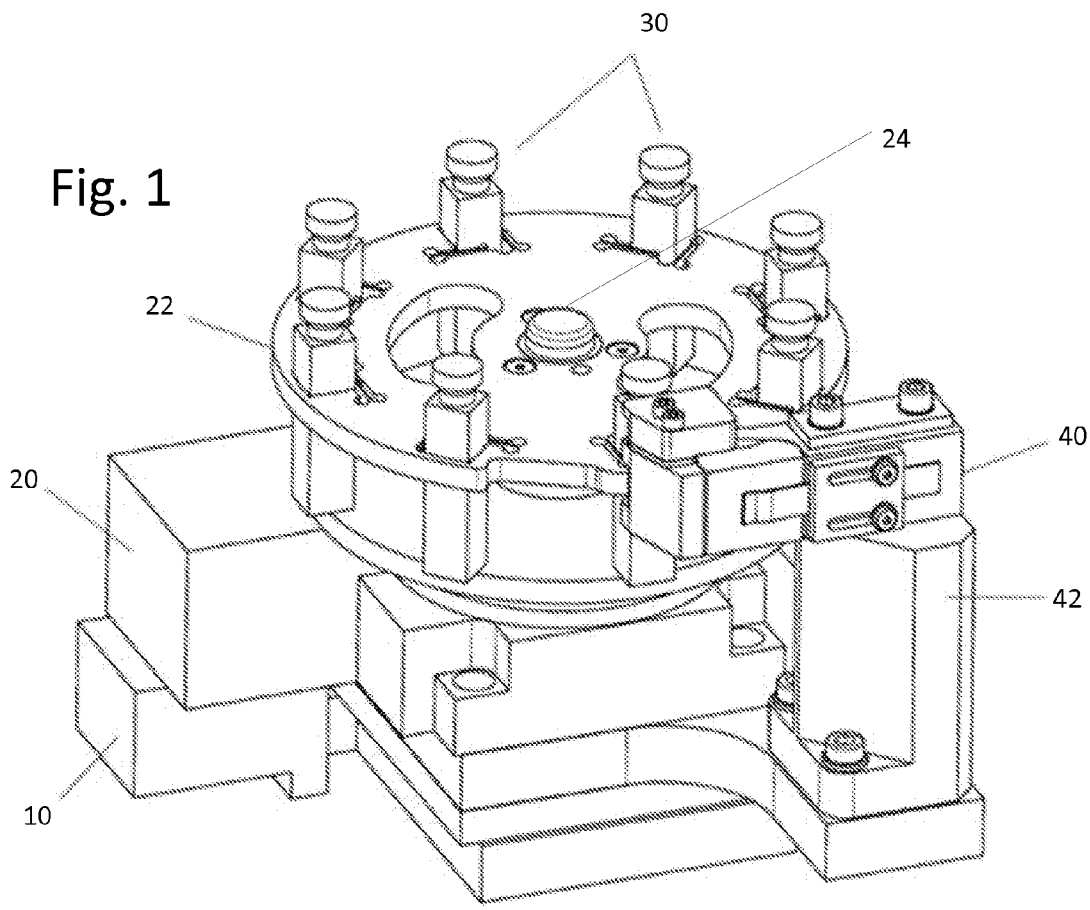
FIG. 1 is a schematic view of the cuvette positioning system showing the carousel carrying multiple cuvettes, the translational stage and the positioning arm in accordance with an embodiment of the present invention.

FIG. 1 illustrates an embodiment of a cuvette positioning system. The cuvette positioning system has motorized translation stage 10 which provides for linear movement of the entire cuvette positioning system. Motorized rotation stage assembly 20 is attached to motorized translation stage 10. Motorized rotation stage assembly 20 uses a motor to position cuvettes 30 around central shaft 24. In this embodiment, cuvettes 30 have a square shape. An individual cuvette 30 is held in precise geometric orientation by cuvette positioning arm 40. Cuvette positioning arm 40 is connected to cuvette positioning arm post 42. Cuvette positioning arm post 42 is further connected to motorized rotation stage assembly 20.

Figure 2A:
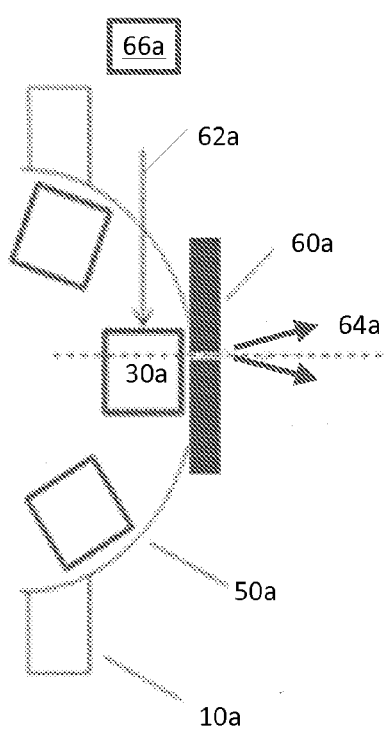
FIG. 2a and FIG. 2b are top view diagrams showing the linear movement of the cuvette positioning system, the direction of light from the excitation source and the corresponding fluorescence emissions through the stationary slit in accordance with an embodiment of the present invention.
Figure 2B:
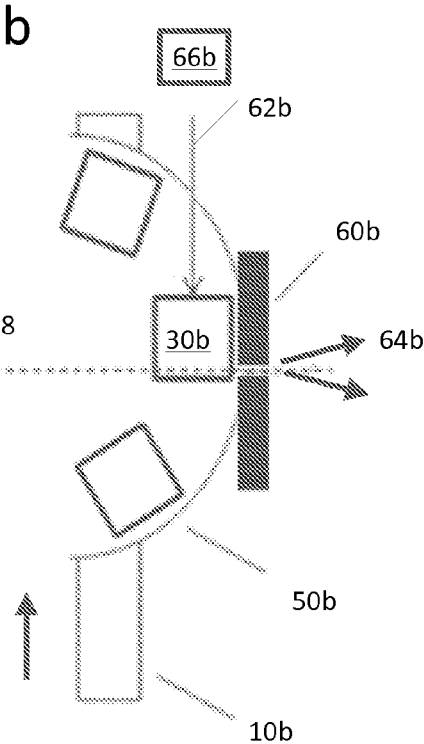

FIGS. 2a and 2b illustrate an embodiment of the cuvette positioning system, showing two positions within the linear movement of the system. In this embodiment, motorized translation stage shown by 10a and 10b has positioned cuvette 30a and 30b in two different linear locations. Cuvette 30a and 30b demonstrates the cuvette being fluoresced by excitation light source 66a and 66b. Excitation light source 66a and 66b generates excitation light beam 62a and 62b, which illuminates the sample in the cuvette 30a and 30b and causes fluorescence emissions 64a and 64b. Fluorescence emissions 64a and 64b are measured as they come out of stationary slit 60a and 60b. Motorized rotation stage assembly is moved linearly by motorized translation stage 10a and 10b in relation to stationary slit 60a and 60b to allow fluorescence emissions measurements to be taken at varying depths of the cuvette 30 contained sample.

Figure 3:
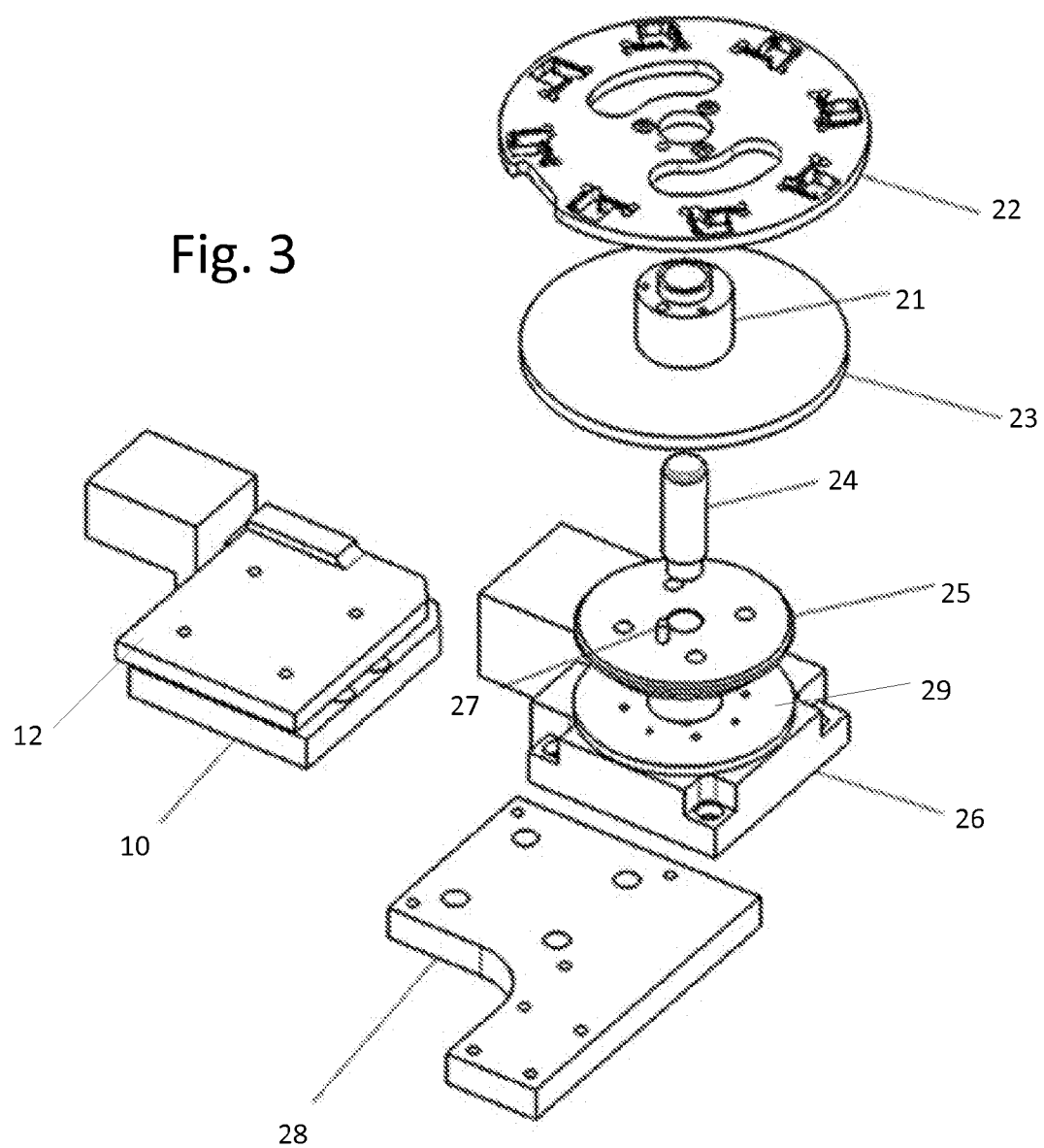
FIG. 3 is an exploded schematic view of the motorized rotation stage assembly without the cuvette positioning arm in accordance with an embodiment of the present invention.

FIG. 3 illustrates an exploded view of the motorized rotation stage assembly with translation stage 10 and without the cuvette positioning arm. Translation stage 10 connects to translation stage platform 12 that provides linear movement substantially along one axis with respect to the light source as described in FIG. 2 above. The motorized rotation stage assembly includes the carousel rotation parts and the cuvette positioning arm assembly, which are both attached to motorized rotation stage assembly connection plate 28. Motorized rotation stage assembly connection plate 28 is further attached to motorized translation stage 10. The carousel rotation parts begin with motorized rotation stage base 26, which houses the motor that rotates the carousel through connected motorized rotation stage top plate 29. Motorized rotation stage top plate 29 attaches to carousel support plate 25 having positioning bolt 27 for alignment with cuvette support plate 23 having connection part 21 that connects to cuvette holder plate 22. Cuvette support plate 23 positioned to rest against each cuvettes lower wall and provide vertical support to the cuvettes. Central shaft 24 goes through the center of the carousel and serves as a central axis about which the carousel revolves. Positioning bolt 27 serves the dual function of allowing the carousel to lit in a predetermined orientation and of providing the means for anchoring the carousel to the rotation stage during rotation. The carousel rotation is driven by a motor in motorized rotation stage base 26 that connects to and is capable of turning the carousel in both directions. The rotation of the carousel allows the carousel contained cuvettes, as shown in FIG. 1, to rotate into a precise position set up to be illuminated by a fixed position light source, as shown in FIG. 2.

Figure 4:
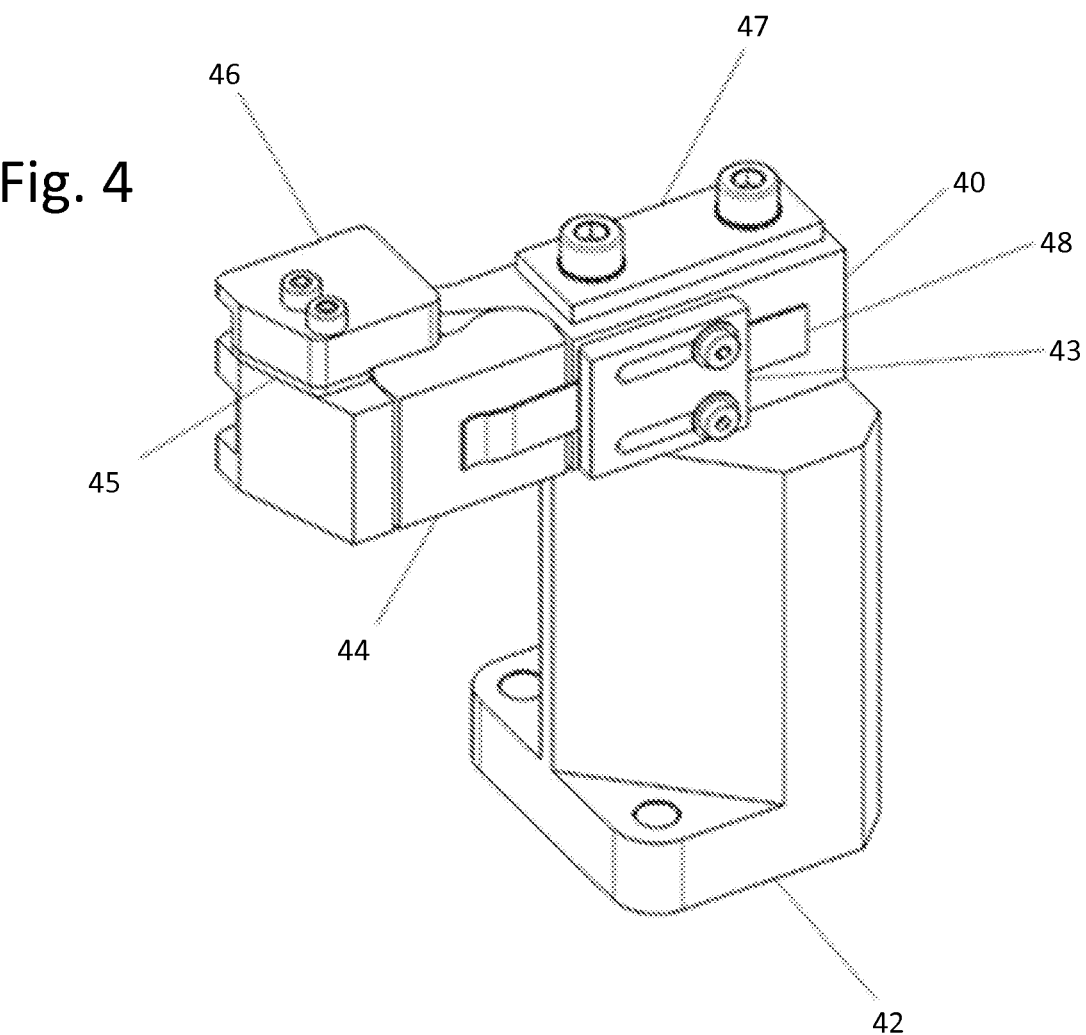
FIG. 4 is a rear schematic view of the cuvette positioning arm and cuvette positioning arm post in accordance with an embodiment of the present invention.

FIG. 4 illustrates another embodiment of the cuvette positioning arm assembly. The cuvette positioning arm assembly consists of cuvette positioning arm 40 connected to cuvette positioning arm post 42. The cuvette positioning arm assembly bolts to motorized rotation stage assembly connection plate 28 as illustrated in FIG. 1. This connection allows the cuvette positioning arm assembly to move together with the carousel using the linear stage. Continuing with FIG. 4, cuvette positioning arm 40 has numerous components to aid in the precise positioning of cuvettes. Lip spring 48 is held in place by lip spring holder plate 43. Lip spring 48 allows positioning lip 44 to pivot away from and then back towards the carousel when the cuvette in the carousel slides in front of positioning lip 44 on its way to being locked in the accurate position for measurement. Lip spring 48 achieves this movement by applying tension against positioning lip 44 so that when a cuvette in the carousel slides in front of positioning lip 44, positioning lip 44 is under greater tension from lip spring 48 such that positioning lip 44 moves back towards the carousel as the cuvette slides past positioning lip 44. Cuvette spacer plate 45 sits between cuvette positioning arm 40 and cuvette end stop 46. Cuvette end stop 46 prevents the active cuvette in the testing position of the carousel from moving upwards once locked into place by cuvette positioning arm 40. Cuvette spacer plate 45 advantageously allows for cuvettes of varying heights to be used in the system. Cuvette arm holder plate 47 serves to attach cuvette positioning arm 40 to cuvette positioning arm post 42.

Figure 5:
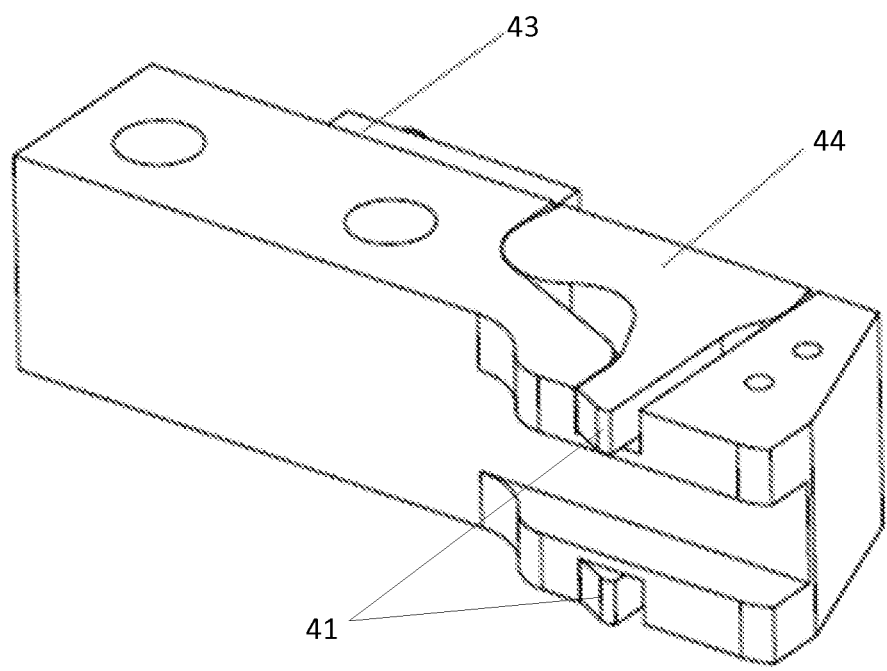
FIG. 5 is a front schematic view of the cuvette positioning arm in accordance with an embodiment of the present invention.

FIG. 5 illustrates a front view of the positioning arm assembly described in FIG. 4. Positioning arm 40 is shown without the cuvette spacer plate, cuvette end stop and cuvette arm holder plate that were described and shown in FIG. 4. A front view shows the unique shape of positioning lip 44 that allows for the accurate positioning of an individual cuvette. The positioning lip 44 has two tongues 41 on a front side of the positioning lip 44 and a rounded edge on a lateral side of the positioning lip 44. The positioning piece is attached to the bulk of the positioning arm in a manner that leaves the two tongues 41 protruding at the front of the positioning lip 44. The two tongues 41 act as a vertical border which aligns one of the four sidewalk of the cuvette. The rounded edge of the positioning lip 44 acts as a hinge about which the positioning lip rotates when it becomes pivoted away from the carousel.

Figure 6:
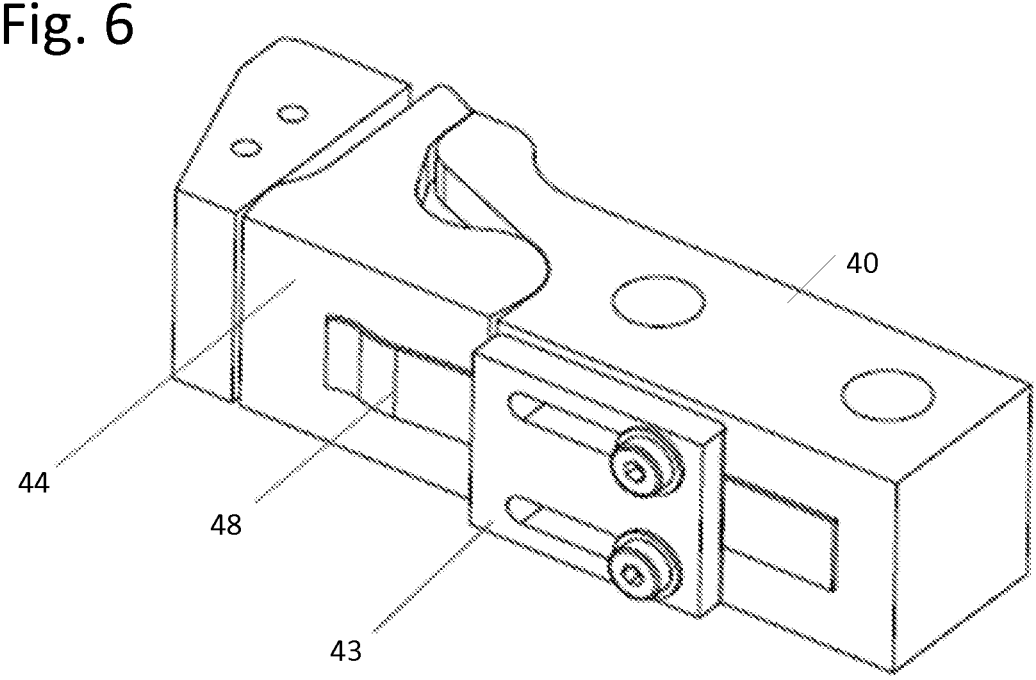
FIG. 6 is a rear schematic view of the cuvette positioning arm in accordance with an embodiment of the present invention.

FIG. 6 illustrates a rear view of the positioning arm assembly described in FIG. 4. Positioning arm 40 is shown without the cuvette spacer plate, cuvette end stop and cuvette arm holder plate. A rear view shows the unique shape of positioning lip 44. Lip holder plate 43 holds lip spring 48 in place which provides tension against positioning lip 44.

Figure 7:
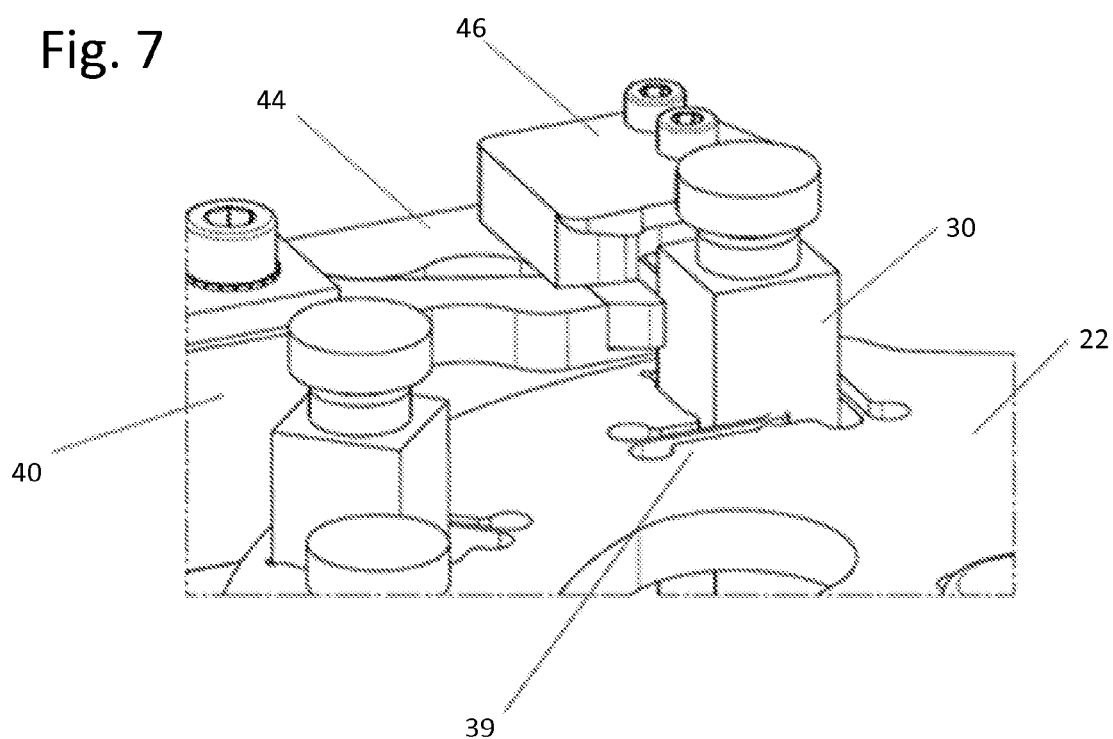
FIG. 7 is a schematic view showing the fitment of a cuvette as positioned in the carousel and held by the cuvette positioning arm in accordance with an embodiment of the present invention.

FIG. 7 illustrates a front view of the cuvette positioning arm assembly holding the active cuvette in the testing position of the carousel in a precise geometric position for measurement. Cuvette 30 is held in place by the cuvette positioning arm assembly as described previously. Cuvette end stop 46 prevents upward movement of the cuvette, helping maintain the precise geometric position the cuvette positioning arm seeks to achieve. Cuvette positioning lip 44 is held by cuvette positioning arm 40 and tensioned by the lip spring, not shown, against cuvette 30. The particular shape of positioning lip 44 determines the precise geometric position of the cuvette in relation to the incoming excitation light beam. Cuvette holder plate 22 has flexible springs 39 that allow for the varying positions that would be imposed by a cuvette positioning tip having a different tongue shape. Flexible springs 39 can be rectangular in shape, sit flush with cuvette holder plate 22, engage with the sides of the cuvette sitting in cuvette holder plate 22 and serve to bias the position of cuvettes to a substantially perpendicular position in relation to cuvette holder plate 22. Over time, flexible springs 39 of cuvette holder plate 22 may weaken and allow more movement of individual cuvettes within cuvette holder plate 22. In regard to the potential added movement of individual cuvettes within the carousel, precise geometric positioning can still be achieved for cuvettes undergoing measurement as described in regard to FIG. 4 by the cuvette positioning arm assembly.

Figure 8:
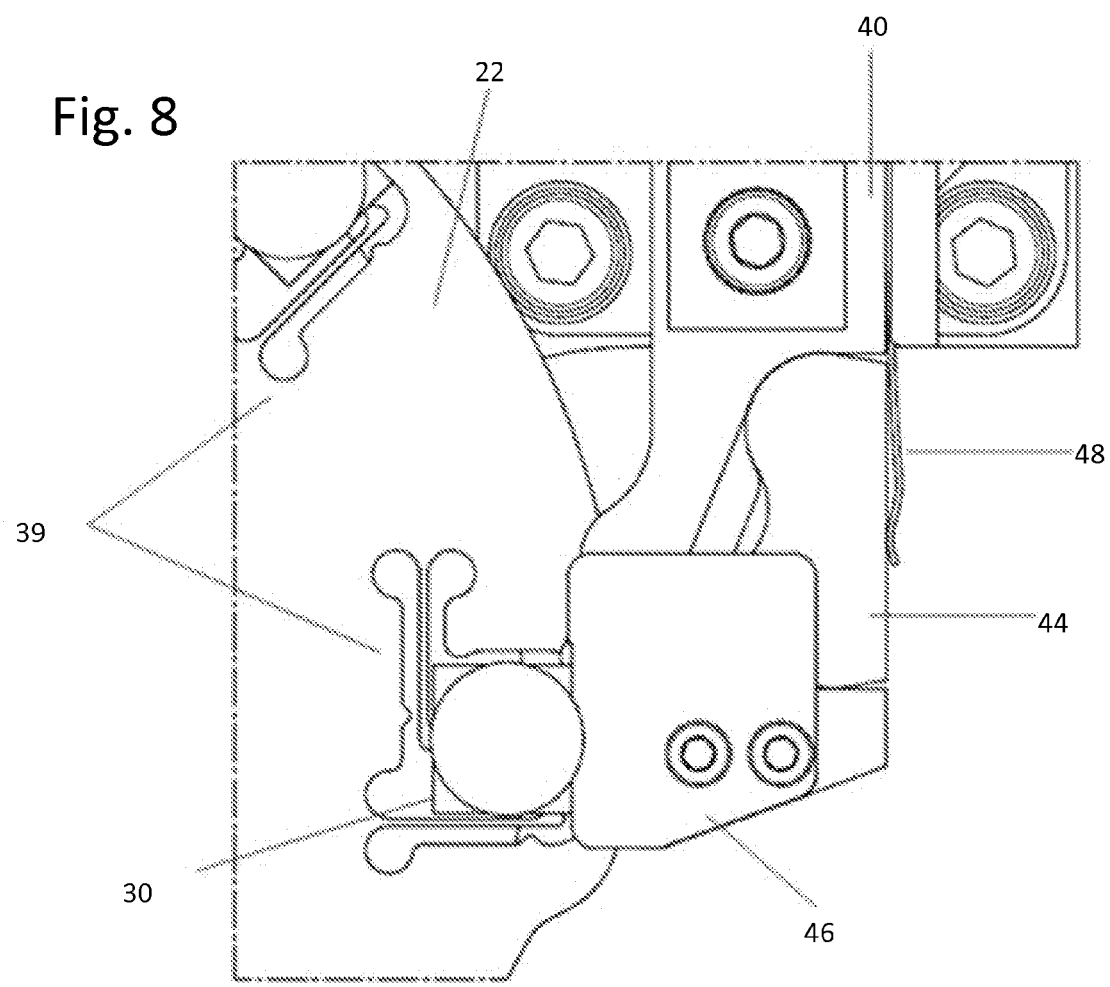
FIG. 8 is a schematic top view showing a cuvette as positioned in the carousel and held by the cuvette positioning arm in accordance with an embodiment of the present invention.

FIG. 8 illustrates a top view of the embodiment described in FIG. 7 above. Cuvette 30 is held in place by the cuvette positioning arm assembly as described previously. Cuvette end stop 46 prevents upward movement of cuvette 30. Cuvette positioning lip 44 is held by cuvette positioning arm 40 and tensioned by lip spring 48 against cuvette 30.

The operation of an embodiment of the cuvette positioning system proceeds as follows in regard to the positioning arm assembly as described in FIGS. 1-8: the carousel carrying the cuvettes rotates clockwise to switch next in line cuvette into the measurement position. As the individual cuvette to be measured reaches and presses on the protruding tongues 41 of the described positioning lip 44, it causes the positioning lip 44 to pivot away from the carousel allowing the cuvette to pass over the protruding tongues 41. After the new cuvette crosses to the lateral side of the tongues 41, the carousel is made to rotate counterclockwise at a small angle until one side of the cuvette touches and slightly presses on the tongues 41 from the lateral side. The unique design of the positioning lip 44 constrains the cuvette from pivoting backward when the tongues 41 are pressed from the lateral side, this causes the cuvette to be cornered parallel to the tongues 41. The way the cuvette is cornered against the lateral side of the tongues 41 provides the sought optically precise orientation of the cuvette for measurement. In an embodiment the portion of the tongues 41 that contact the cuvettes may be substantially parallel to carousel central shaft 24 such that the cuvettes are cornered substantially parallel to central shaft 24. In another embodiment the portion of the tongues 41 that contact the cuvettes may be angled or each tongue can be offset from each other such that the cuvettes are cornered at a precise angle in relation to the carousel central shaft 24. When the cuvette is in the measurement position depth-resolved laser induced fluorescence or other photo-optical measurements may be performed to the cuvette contained sample. The cuvette can be transparent such that the laser can enter the cuvette and cause fluorescence emissions to emit off of the sample and out of the transparent cuvette towards measuring devices. In an embodiment these emissions can be measured through a substantially stationary slit as described in FIG. 2 or by other techniques.

In addition to depth-resolved laser-induced fluorescence measurements, the described embodiment could also be adapted for other photo-optical measurements such as absorption, transmission and interferometry.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, language referring to order, such as first and second, should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

What is claimed is:

1. A cuvette positioning system comprising:
   a motorized rotation stage assembly having a rotatable carousel assembly and a positioning arm assembly, the motorized rotation stage assembly having a motorized translation stage to linearly position the motorized rotation stage assembly in relation to an excitation light source;
   the rotatable carousel assembly having a plurality of cuvettes around a central shaft, each cuvette of the plurality of cuvettes having a lower wall, an upper wall, a plurality of sidewalls, an opening, and a cavity;
   the plurality of cuvettes positioned in a cuvette holder plate within the carousel assembly, the cuvette holder plate having a plurality of flexible spring tension arms set against the plurality of sidewalls of the plurality of cuvettes, the plurality of spring tension arms biasing the sidewalls of each of the plurality of cuvettes towards a position substantially parallel with the central shaft, thereby preparing the position of each cuvette of the plurality of cuvettes such that when the rotatable carousel assembly rotates an individual cuvette of the plurality of cuvettes to a testing location, the cuvette positioning arm assembly can engage the individual cuvette;
   the cuvette positioning arm assembly having a cuvette positioning arm connected to a cuvette positioning arm post, the cuvette positioning arm aligning an individual cuvette of the plurality of cuvettes in a particular measurement position such that the plurality of cuvette sidewalls are at a particular measurement angle, thereby setting the position of the individual cuvette in the testing location such that the particular position of the individual cuvette is repeatable for each individual cuvette of the plurality of cuvettes when the each individual cuvette is placed into the testing location by the rotatable carousel assembly; and
   a cuvette positioning lip connected to the cuvette positioning arm wherein the cuvette positioning lip has a plurality of tongues.

2. The system of claim 1, further comprising;
   cuvette support plate connected to the motorized rotation stage assembly and positioned to rest against the lower wall of each of the plurality of cuvettes, thereby supporting the lower wall of each cuvette in the motorized rotation stage assembly and maintaining the vertical position of each cuvette of the plurality of cuvettes within the cuvette holder plate.

3. The system of claim 1, further comprising:
   a lip spring having a lip spring holder plate connected to the cuvette positioning arm, the lip spring holder plate pressing against the cuvette positioning arm.

4. The system of claim 1, wherein the lip spring presses the tongues of the cuvette positioning lip against the cuvette positioned by the cuvette positioning arm assembly, thereby causing the cuvette to be cornered against the tongues in a particular position.

5. The system of claim 1, further comprising:
   a cuvette end stop connected to the cuvette positioning arm assembly positioned to prevent upward movement of the cuvette positioned by the cuvette positioning arm assembly.

6. The system of claim 1, wherein the excitation light source comprises a laser.

7. A cuvette positioning apparatus comprising:
a rotatable carousel assembly having a plurality of cuvettes around a motorized central shaft;
the plurality of cuvettes positioned in a cuvette holder plate such that a plurality of cuvette walls of each of the plurality of cuvettes contact the cuvette holder plate, the cuvette holder plate connected to the motorized central shaft, thereby allowing the cuvette holder plate to rotate each of the cuvettes of the plurality of cuvettes around the motorized central shaft and into a testing position;
a cuvette positioning arm assembly having a cuvette positioning arm connected to a cuvette positioning arm post located adjacent the testing position, the cuvette positioning arm aligning an individual cuvette of the plurality of cuvettes in a particular measurement position that is repeatable for each individual cuvette in the plurality of cuvettes when the each individual cuvette is rotated into the testing position; and
a lip spring and a lip spring holder connected to the cuvette positioning arm; and further comprising a cuvette positioning lip connected to the cuvette positioning arm wherein the cuvette positioning lip has a plurality of tongues, the tongues aligning an individual cuvette when the cuvette is being held by the cuvette positioning arm assembly.

8. The system of claim 7, further comprising:
an excitation light source positioned to fluoresce a cuvette positioned by the cuvette positioning arm in the testing position.

9. The system of claim 8, wherein the excitation light source comprises a laser.

10. The system of claim 7, further comprising:
a cuvette support plate connected to the rotatable carousel assembly and positioned against a lower side of each of the plurality of cuvettes to thereby support the cuvettes within the carousel assembly.

11. The system of claim 7, wherein the lip spring presses the tongues of the cuvette positioning lip against the cuvette positioned by the cuvette positioning arm assembly, thereby causing the cuvette to be cornered against the tongues.

12. The system of claim 7, further comprising:
a cuvette end stop connected to the cuvette positioning arm assembly positioned to prevent upward movement of the cuvette positioned by the cuvette positioning arm assembly.

13. A method of positioning cuvettes comprising:
positioning a plurality of cuvettes around a central shaft of a rotatable carousel assembly, the plurality of cuvettes positioned in a cuvette holder plate within the carousel, wherein the cuvette holder plate has flexible spring tension arms positioned against the sides of the plurality of cuvettes;
rotating the rotatable carousel assembly clockwise until a side of an individual cuvette of the plurality of cuvettes presses against a plurality of tongues of a cuvette positioning arm assembly such that the side of the individual cuvette passes over the plurality of tongues; and
rotating the rotatable carousel assembly counterclockwise at a small angle until one side of an individual cuvette of the plurality of cuvettes touches and slightly presses on a plurality of tongues of the cuvette positioning arm assembly causing the individual cuvette to be cornered against the tongues thereby precisely positioning the individual cuvette such that the same position can be substantially repeated for each of the individual cuvettes.

14. The method according to claim 13, further comprising:
fluorescing with an excitation light source, the individual cuvette of the plurality of cuvettes cornered against the tongues by the cuvette positioning arm assembly, thereby causing fluorescence emissions to project from a sample contained in the individual cuvette through a stationary slit positioned adjacent the individual cuvette.

15. The method according to claim 14, further comprising:
linearly positioning, by a motorized translation stage assembly, the rotatable carousel assembly and the positioning arm assembly in relation to the excitation light source.

16. The method according to claim 14, further comprising:
continuing to rotate the rotatable carousel assembly clockwise at a small angle until one side of an individual cuvette of the plurality of cuvettes further presses on the plurality of tongues of the cuvette positioning arm assembly causing the tension of the spring tension arms of the cuvette holder plate to be partially overcome, thereby causing the spring tension arms to flex such that the individual cuvette is rigidly held against the tongues of the cuvette positioning arm.

17. The method according to claim 14, wherein the excitation light source comprises a laser.

* * * * *